(12) United States Patent
El-Tamimy

(10) Patent No.: US 10,973,761 B2
(45) Date of Patent: Apr. 13, 2021

(54) PHARMACEUTICAL FORMULATION

(71) Applicant: Phosphagenics Limited, Clayton (AU)

(72) Inventor: Mahmoud El-Tamimy, Clayton (AU)

(73) Assignee: Phosphagenics Limited, Clayton (AU)

(*) Notice: Subject to any disclaimer, the term of this patent is extended or adjusted under 35 U.S.C. 154(b) by 0 days.

(21) Appl. No.: 16/060,868

(22) PCT Filed: Dec. 9, 2016

(86) PCT No.: PCT/AU2016/051209
§ 371 (c)(1),
(2) Date: Jun. 8, 2018

(87) PCT Pub. No.: WO2017/096427
PCT Pub. Date: Jun. 15, 2017

(65) Prior Publication Data
US 2019/0015329 A1 Jan. 17, 2019

Related U.S. Application Data

(60) Provisional application No. 62/329,166, filed on Apr. 28, 2016.

(30) Foreign Application Priority Data

Dec. 9, 2015 (AU) .................. 2015905089

(51) Int. Cl.
| | | |
|---|---|---|
| A61K 9/00 | (2006.01) | |
| A61K 9/10 | (2006.01) | |
| A61K 9/107 | (2006.01) | |
| A61K 45/06 | (2006.01) | |
| A61K 8/06 | (2006.01) | |
| A61P 23/02 | (2006.01) | |
| A61K 31/05 | (2006.01) | |
| A61K 47/10 | (2017.01) | |
| A61K 47/22 | (2006.01) | |
| A61K 47/26 | (2006.01) | |
| A61K 47/44 | (2017.01) | |

(52) U.S. Cl.
CPC .......... *A61K 9/1075* (2013.01); *A61K 31/05* (2013.01); *A61K 47/10* (2013.01); *A61K 47/22* (2013.01); *A61K 47/26* (2013.01); *A61K 47/44* (2013.01)

(58) Field of Classification Search
CPC ...... A61K 2300/00; A61K 9/10; A61K 9/107; A61P 25/00; A61P 23/00
See application file for complete search history.

(56) References Cited

U.S. PATENT DOCUMENTS

| | | |
|---|---|---|
| 2,407,823 A | 9/1946 | Fieser |
| 2,457,932 A | 1/1949 | Solmssen et al. |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 3,607,765 A | 9/1971 | Wixon |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 4,977,282 A | 12/1990 | Baldwin et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |
| 5,138,084 A | 8/1992 | Casagrande et al. |
| 5,173,304 A | 12/1992 | Lohner et al. |
| 5,334,378 A | 8/1994 | Mitani et al. |
| 5,374,645 A | 12/1994 | Kurihara-Bergstrom et al. |
| 5,387,579 A | 2/1995 | Meybeck et al. |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | Distefano et al. |
| 5,583,105 A | 12/1996 | Kovacs et al. |
| 5,589,504 A | 12/1996 | Dannenberg et al. |

(Continued)

FOREIGN PATENT DOCUMENTS

| | | |
|---|---|---|
| CA | 1337992 C | 1/1996 |
| CA | 2426852 A1 | 5/2002 |

(Continued)

OTHER PUBLICATIONS

Baker et al. Propofol. Oct. 2005. Anesthesiology. vol. 103. pp. 860-876. (Year: 2005).*
International Search Report, PCT/AU2016/051209, dated Feb. 2, 2017.
International Preliminary Report on Patentability, PCT/AU2016/051209, dated Mar. 22, 2018.
Aberg, F. et al., "Distribution and redox state of ubiquinones in rat and human tissues," Arch. Biochem. Biophys. (1992) 295(2):230-234.
Advantages of Liposomal Delivery Systems for Anthracyclines, Semin. Oncol., 2004, 6 Suppl 13, 5-15.
Almeida, M.E.M. et al., "Evaluation of soybean oil deodorization distillate for Vitamin E recovery," Arq. Biol. Tecnol. (1994) 37(4):1003-1011.

(Continued)

*Primary Examiner* — Tracy Liu
(74) *Attorney, Agent, or Firm* — Michael Best & Friedrich LLP

(57) ABSTRACT

The present invention relates to a formulation comprising a primary surfactant, a tocol phosphate, water, an active agent, and optionally an oil, wherein the active agent and/or the optional oil comprises a hydrophobic phase.

3 Claims, No Drawings

(56) References Cited

U.S. PATENT DOCUMENTS

| | | | |
|---|---|---|---|
| 5,603,949 A | 2/1997 | Meybeck et al. | |
| 5,607,921 A | 3/1997 | Bernard et al. | |
| 5,643,597 A | 7/1997 | Meybeck et al. | |
| 5,656,618 A | 8/1997 | Meybeck et al. | |
| 5,656,672 A | 8/1997 | Collin et al. | |
| 5,741,518 A | 4/1998 | Ribier et al. | |
| 5,759,526 A | 6/1998 | Simonnet et al. | |
| 5,776,915 A | 7/1998 | Peterson et al. | |
| 5,780,504 A | 7/1998 | Ptchelintsev | |
| 5,804,168 A | 9/1998 | Murad | |
| 5,804,216 A | 9/1998 | Terren et al. | |
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A | 7/1999 | Lucas et al. | |
| 5,952,361 A | 9/1999 | Dias Nahoum | |
| 5,952,373 A | 9/1999 | Lanzendorfer et al. | |
| 5,965,750 A | 10/1999 | Oonishi et al. | |
| 5,981,474 A | 11/1999 | Manning et al. | |
| 5,985,856 A | 11/1999 | Stella et al. | |
| 6,022,867 A | 2/2000 | Ito et al. | |
| 6,028,105 A | 2/2000 | Nigra | |
| 6,046,181 A | 4/2000 | Oonishi et al. | |
| 6,048,891 A | 4/2000 | Wechter | |
| 6,096,326 A | 8/2000 | Wikholm | |
| 6,121,249 A | 9/2000 | Weissman et al. | |
| 6,143,770 A | 11/2000 | Lane et al. | |
| 6,184,247 B1 | 2/2001 | Schneider | |
| 6,231,885 B1 | 5/2001 | Carrara | |
| 6,248,758 B1 | 6/2001 | Klokkers et al. | |
| 6,248,779 B1 | 6/2001 | Shimizu et al. | |
| 6,361,800 B1 | 3/2002 | Cooper et al. | |
| 6,384,043 B1 | 5/2002 | Peyman et al. | |
| 6,403,811 B1 | 6/2002 | West | |
| 6,417,223 B1 | 7/2002 | Sanders et al. | |
| 6,423,742 B1 | 7/2002 | Larson | |
| 6,444,220 B2 | 9/2002 | Wiley | |
| 6,444,234 B1 | 9/2002 | Kirby et al. | |
| 6,479,540 B1 | 11/2002 | Constantinides et al. | |
| 6,485,950 B1 | 11/2002 | Kumar et al. | |
| 6,503,545 B1 | 1/2003 | Perlman et al. | |
| 6,579,995 B1 | 6/2003 | West | |
| 6,599,933 B2 | 7/2003 | Takata et al. | |
| 6,641,847 B1 | 11/2003 | Nawar | |
| 6,645,998 B2 | 11/2003 | Sanders et al. | |
| 6,703,384 B2 | 3/2004 | Sanders et al. | |
| 6,727,280 B2 | 4/2004 | Paiepu et al. | |
| 6,770,672 B1 | 8/2004 | Sanders et al. | |
| 6,887,648 B2 | 5/2005 | Pavelchek et al. | |
| 7,074,825 B2 | 7/2006 | Mo et al. | |
| 7,179,486 B1 | 2/2007 | Mulye | |
| 7,648,710 B2 | 1/2010 | West | |
| 8,008,345 B2 | 8/2011 | West et al. | |
| 8,529,947 B2 | 9/2013 | West et al. | |
| 8,546,453 B2 * | 10/2013 | Zhang | A61K 9/0019 424/450 |
| 8,652,511 B2 | 2/2014 | Cottrell et al. | |
| 9,314,527 B2 | 4/2016 | Cottrell et al. | |
| 9,561,243 B2 | 2/2017 | Libinaki | |
| 2001/0006659 A1 | 7/2001 | Koike et al. | |
| 2001/0044462 A1 | 11/2001 | Hensley et al. | |
| 2002/0045765 A1 | 4/2002 | Kim et al. | |
| 2002/0127198 A1 | 9/2002 | Rothbard et al. | |
| 2002/0131994 A1 | 9/2002 | Schur et al. | |
| 2002/0132845 A1 | 9/2002 | Miller et al. | |
| 2002/0151467 A1 | 10/2002 | Leung | |
| 2003/0035812 A1 | 2/2003 | Ito et al. | |
| 2003/0109575 A1 | 6/2003 | Lambert et al. | |
| 2003/0157326 A1 | 8/2003 | Vaghefi et al. | |
| 2003/0206972 A1 | 11/2003 | Babish et al. | |
| 2003/0220301 A1 | 11/2003 | Lal et al. | |
| 2004/0052745 A1 | 3/2004 | Bernard et al. | |
| 2004/0052754 A1 | 3/2004 | West et al. | |
| 2004/0062817 A1 | 4/2004 | Peshoff | |
| 2004/0067890 A1 | 4/2004 | Gupta | |
| 2004/0097431 A1 | 5/2004 | Sanders et al. | |
| 2004/0097472 A1 | 5/2004 | West et al. | |
| 2004/0102385 A1 | 5/2004 | Ames et al. | |
| 2004/0131569 A1 | 7/2004 | Schneider et al. | |
| 2004/0167081 A1 | 8/2004 | Abbruzzese et al. | |
| 2004/0204343 A1 | 10/2004 | Fishman | |
| 2004/0234602 A1 | 11/2004 | Fischer et al. | |
| 2004/0235938 A1 | 11/2004 | Sanders et al. | |
| 2004/0241225 A1 | 12/2004 | West | |
| 2005/0009787 A1 | 1/2005 | West et al. | |
| 2005/0089495 A1 | 4/2005 | West et al. | |
| 2005/0134664 A1 | 6/2005 | Pavlin | |
| 2005/0142174 A1 | 6/2005 | Assmus et al. | |
| 2005/0220733 A1 | 10/2005 | Tsuzuki et al. | |
| 2006/0120979 A1 | 6/2006 | Rubin | |
| 2006/0228395 A1 | 10/2006 | Lamb et al. | |
| 2006/0241085 A1 | 10/2006 | West et al. | |
| 2006/0257459 A1 | 11/2006 | West et al. | |
| 2006/0281715 A1 | 12/2006 | West | |
| 2006/0281716 A1 | 12/2006 | West et al. | |
| 2007/0042999 A1 | 2/2007 | West et al. | |
| 2007/0110739 A1 | 5/2007 | Logsdon | |
| 2007/0135390 A1 | 6/2007 | West et al. | |
| 2007/0141090 A1 | 6/2007 | Harris et al. | |
| 2007/0141133 A1 | 6/2007 | Wang et al. | |
| 2007/0224253 A1 | 9/2007 | Franklin | |
| 2008/0233178 A1 | 9/2008 | Reidenberg et al. | |
| 2008/0254073 A1 | 10/2008 | Chi | |
| 2008/0299100 A1 | 12/2008 | Hsia et al. | |
| 2009/0004166 A1 | 1/2009 | West et al. | |
| 2009/0005348 A1 | 1/2009 | Ogru et al. | |
| 2009/0036354 A1 * | 2/2009 | Gavin | A61K 8/34 514/1.1 |
| 2009/0104258 A1 | 4/2009 | Dumas et al. | |
| 2009/0186856 A1 | 7/2009 | West et al. | |
| 2009/0233881 A1 | 9/2009 | West et al. | |
| 2009/0239827 A1 | 9/2009 | Ogru et al. | |
| 2009/0274677 A1 | 11/2009 | Isaacs et al. | |
| 2009/0319191 A1 | 12/2009 | Rivas et al. | |
| 2009/0325953 A1 | 12/2009 | Sahoo et al. | |
| 2009/0325974 A1 | 12/2009 | Eggenweiler et al. | |
| 2010/0034880 A1 * | 2/2010 | Sintov | A61K 9/0014 424/484 |
| 2010/0076094 A1 | 3/2010 | West et al. | |
| 2010/0222305 A1 | 9/2010 | West et al. | |
| 2010/0261670 A1 | 10/2010 | West et al. | |
| 2011/0003774 A1 | 1/2011 | West et al. | |
| 2012/0202780 A1 | 8/2012 | Gavin et al. | |
| 2012/0283233 A1 | 11/2012 | Gavin et al. | |
| 2012/0321604 A1 | 12/2012 | Libinaki | |
| 2014/0322330 A1 * | 10/2014 | Chiragkumar | A61K 9/0014 424/489 |
| 2016/0184436 A1 | 6/2016 | Cottrell et al. | |
| 2016/0331838 A1 | 11/2016 | Gavin et al. | |
| 2016/0375136 A1 | 12/2016 | Gavin et al. | |
| 2017/0112863 A1 | 4/2017 | Libinaki et al. | |

FOREIGN PATENT DOCUMENTS

| | | |
|---|---|---|
| CA | 2426885 A1 | 5/2002 |
| CN | 1600297 A | 3/2005 |
| CN | 1917858 A | 2/2007 |
| CN | 101524330 A | 9/2009 |
| EP | 0171009 B1 | 2/1986 |
| EP | 0324387 B1 | 7/1989 |
| EP | 0338429 B1 | 10/1989 |
| EP | 0430045 B1 | 6/1991 |
| EP | 0430336 B1 | 6/1991 |
| EP | 0436911 A2 | 7/1991 |
| EP | 0565007 B1 | 10/1993 |
| EP | 0574255 B1 | 12/1993 |
| EP | 0612521 A1 | 8/1994 |
| EP | 0617963 B1 | 10/1994 |
| EP | 0641790 A1 | 3/1995 |
| EP | 0643969 B1 | 3/1995 |
| EP | 0650721 A1 | 5/1995 |

(56) References Cited

FOREIGN PATENT DOCUMENTS

| | | |
|---|---|---|
| EP | 0661053 A1 | 7/1995 |
| EP | 0669132 A1 | 8/1995 |
| EP | 0674904 A1 | 10/1995 |
| EP | 0679399 B1 | 11/1995 |
| EP | 0680760 A1 | 11/1995 |
| EP | 0681840 B1 | 11/1995 |
| EP | 0684043 A1 | 12/1995 |
| EP | 0699437 A1 | 3/1996 |
| EP | 0699440 A1 | 3/1996 |
| EP | 0826365 A2 | 3/1998 |
| EP | 0845216 A1 | 6/1998 |
| EP | 0699437 B1 | 12/1998 |
| EP | 0965328 A1 | 12/1999 |
| EP | 1000541 B1 | 5/2000 |
| EP | 1023897 A2 | 8/2000 |
| EP | 1053749 A1 | 11/2000 |
| EP | 1264595 A1 | 12/2002 |
| EP | 1470817 A1 | 10/2004 |
| EP | 1783209 B1 | 5/2007 |
| EP | 102079756 B | 9/2012 |
| FR | 2777179 A1 | 10/1999 |
| GB | 778142 A | 7/1957 |
| GB | 1121683 A | 7/1968 |
| GB | 2227662 A | 8/1990 |
| JP | 50022535 A | 3/1975 |
| JP | 52039013 | 3/1977 |
| JP | 53015381 | 2/1978 |
| JP | 58180410 A | 10/1983 |
| JP | 59044375 A | 3/1984 |
| JP | 59157091 A | 9/1984 |
| JP | 60197621 A | 10/1985 |
| JP | 61086940 A | 5/1986 |
| JP | 61091137 A | 5/1986 |
| JP | 61176535 A | 8/1986 |
| JP | 61233631 A | 10/1986 |
| JP | 62195393 A | 8/1987 |
| JP | 63093791 A | 4/1988 |
| JP | 63139972 A | 6/1988 |
| JP | 1228920 A | 9/1989 |
| JP | 1274830 A | 11/1989 |
| JP | 03-072426 A | 3/1991 |
| JP | 03-120230 A | 5/1991 |
| JP | 4208209 A | 7/1992 |
| JP | 4270212 A | 9/1992 |
| JP | 05-000946 A | 1/1993 |
| JP | 5132700 B2 | 5/1993 |
| JP | 5201858 A | 8/1993 |
| JP | 6048962 A | 2/1994 |
| JP | 6056699 A | 3/1994 |
| JP | 6078214 B | 10/1994 |
| JP | 7011291 A | 1/1995 |
| JP | 7207298 A | 8/1995 |
| JP | 7278587 A | 10/1995 |
| JP | 7316170 A | 12/1995 |
| JP | 8073338 A | 3/1996 |
| JP | 8193089 A | 7/1996 |
| JP | 08-231564 A | 9/1996 |
| JP | 8311085 A | 11/1996 |
| JP | 8311489 A | 11/1996 |
| JP | 8325594 A | 12/1996 |
| JP | 9044375 A | 2/1997 |
| JP | 9309813 A | 12/1997 |
| JP | 10045783 A | 2/1998 |
| JP | 10155429 A | 6/1998 |
| JP | 10509451 T | 9/1998 |
| JP | 10511677 T | 11/1998 |
| JP | 11043436 A | 2/1999 |
| JP | 11506419 T | 6/1999 |
| JP | 11199424 A | 7/1999 |
| JP | 11199465 A | 7/1999 |
| JP | 2000198701 A | 7/2000 |
| JP | 2001169731 A | 6/2001 |
| JP | 2001247585 A | 9/2001 |
| JP | 2002080475 A | 3/2002 |
| JP | 2002088091 A | 3/2002 |
| JP | 2003128531 A | 5/2003 |
| JP | 2003171313 A | 6/2003 |
| JP | 2006143660 A | 6/2008 |
| NZ | 244549 | 7/1994 |
| RU | 2266121 C2 | 12/2005 |
| RU | 2296743 C2 | 4/2007 |
| RU | 2302857 C2 | 7/2007 |
| RU | 2373957 C2 | 11/2009 |
| RU | 2009125613 A | 1/2011 |
| SU | 925961 | 5/1982 |
| UA | 29476 C2 | 11/2000 |
| WO | WO 91/17987 A1 | 11/1991 |
| WO | WO 92/03122 A1 | 3/1992 |
| WO | WO 92/07544 A1 | 5/1992 |
| WO | WO 92/08459 A1 | 5/1992 |
| WO | WO 92/15289 A1 | 9/1992 |
| WO | WO 93/02661 A1 | 2/1993 |
| WO | WO 93/09768 A1 | 5/1993 |
| WO | WO 93/15731 A1 | 8/1993 |
| WO | WO 93/24131 A1 | 12/1993 |
| WO | WO 95/31217 A1 | 11/1995 |
| WO | WO 95/34303 A1 | 12/1995 |
| WO | WO 96/17852 A1 | 6/1996 |
| WO | WO 96/20715 A1 | 7/1996 |
| WO | WO 96/21440 A1 | 7/1996 |
| WO | WO 96/29336 A1 | 9/1996 |
| WO | WO 96/37196 A1 | 11/1996 |
| WO | WO 97/02803 A1 | 1/1997 |
| WO | WO 97/14705 A1 | 4/1997 |
| WO | WO 97/35591 A2 | 10/1997 |
| WO | 1998030205 A1 | 7/1998 |
| WO | WO 99/35242 A1 | 7/1999 |
| WO | WO 99/58555 A2 | 11/1999 |
| WO | WO 00/08033 A1 | 2/2000 |
| WO | WO 00/16772 A1 | 3/2000 |
| WO | WO 00/30620 A1 | 6/2000 |
| WO | WO 00/43380 A1 | 7/2000 |
| WO | 2000/048571 A1 | 8/2000 |
| WO | WO 00/44237 A2 | 8/2000 |
| WO | WO 00/44375 A1 | 8/2000 |
| WO | WO 00/53728 A2 | 9/2000 |
| WO | WO 00/57876 A1 | 10/2000 |
| WO | WO 00/59475 A1 | 10/2000 |
| WO | WO 00/69865 A1 | 11/2000 |
| WO | WO 00/71094 A1 | 11/2000 |
| WO | WO 00/71125 A2 | 11/2000 |
| WO | WO 00/74684 A1 | 12/2000 |
| WO | WO 01/13901 A2 | 3/2001 |
| WO | WO 01/19372 A1 | 3/2001 |
| WO | WO 01/22937 A1 | 4/2001 |
| WO | WO 01/35883 A1 | 5/2001 |
| WO | WO 01/35998 A1 | 5/2001 |
| WO | WO 01/46204 A1 | 6/2001 |
| WO | WO 01/54674 A1 | 8/2001 |
| WO | WO 01/58889 A1 | 8/2001 |
| WO | WO 01/072300 A1 | 10/2001 |
| WO | WO 02/02385 A1 | 1/2002 |
| WO | WO 02/13810 A1 | 2/2002 |
| WO | WO 02/26238 A1 | 4/2002 |
| WO | 2002040033 A1 | 5/2002 |
| WO | WO 02/3996 A2 | 5/2002 |
| WO | WO 02/36736 A2 | 5/2002 |
| WO | WO 02/40034 A1 | 5/2002 |
| WO | 2002045709 A1 | 6/2002 |
| WO | WO 2002/096217 A1 | 12/2002 |
| WO | WO 03/011303 A1 | 2/2003 |
| WO | WO 03/013550 A1 | 2/2003 |
| WO | WO 03/024429 A1 | 3/2003 |
| WO | WO 03/024430 A1 | 3/2003 |
| WO | WO 03/026673 A1 | 4/2003 |
| WO | WO 03/0039461 A2 | 5/2003 |
| WO | WO 03/043570 A1 | 5/2003 |
| WO | WO 03/049774 A1 | 6/2003 |
| WO | WO 03/053407 A1 | 7/2003 |
| WO | WO 03/068209 A1 | 8/2003 |
| WO | WO 03/097714 A1 | 11/2003 |
| WO | WO 03/101480 A1 | 12/2003 |
| WO | 2004010941 A2 | 2/2004 |
| WO | WO 2004/014432 A1 | 2/2004 |

(56) References Cited

FOREIGN PATENT DOCUMENTS

| WO | WO 2004/060315 A2 | 7/2004 |
|---|---|---|
| WO | WO 2004/064831 A1 | 8/2004 |
| WO | WO 2004/091636 A1 | 10/2004 |
| WO | WO 2004/092186 A1 | 10/2004 |
| WO | WO 2004/092187 A1 | 10/2004 |
| WO | WO 2005/023282 A1 | 3/2005 |
| WO | 2005084678 A1 | 9/2005 |
| WO | WO 2006/012692 A1 | 2/2006 |
| WO | WO 2006/041506 A2 | 4/2006 |
| WO | WO 2006/092024 A1 | 9/2006 |
| WO | WO 2006/092025 A1 | 9/2006 |
| WO | WO 2006/133506 A1 | 12/2006 |
| WO | WO 2007/070981 A1 | 6/2007 |
| WO | WO 2007/075883 A2 | 7/2007 |
| WO | WO 2008/034178 A1 | 3/2008 |
| WO | 2008/073731 A2 | 6/2008 |
| WO | WO 2009/146443 A1 | 12/2009 |
| WO | 2011075775 A1 | 6/2011 |
| WO | WO 2011/094814 A1 | 8/2011 |
| WO | WO 2013/066400 A1 | 5/2013 |

OTHER PUBLICATIONS

Anslyn, E.V. et al., Modern Physical Organic Chemistry. Chapter 3: Solutions and Non-Covalent Binding Forces. University Science Books. (2006) see p. 146.

Barrett, C.W. et al., "The effect of particle size and vehicle on the percutaneous absorption of fluocinolone acetonide," Brit. J. Dermatol. (1965) 77:576-578.

Barry, "Novel mechanisms and devices to enable successful transdermal drug delivery." Sciences, 2001; 14:101-114.

Berge et al., "Journal Pharmaceutical Sciences," 66:1-19, 1977.

Bikerman, J.J., "Mechanical destruction of young and old foam films," J. Phys. Chem. (1952) 56:164-165.

Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.

Blom, J.H. et al., "Reproductive success of female rainbow trout (*Oncorhynchus mykiss*) in response to graded dietary ascorbyl monophosphate levels," Biol. of Reproduction (1995) 52:1073-1080.

Blum, A. et al., "Clinical and inflammatory effects of dietary L-arginine in patients with intractable angina pectoris," Amer. J. Cardiol. (1999) 1488-1489.

Brandt, M., "Steroid hormone biosynthesis," (2002) printed from http://www.rose_hulman.edu/~brandt/Chem430/Steroids.pdf on Nov. 20, 2010 (7 pages).

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998). 1368:201-215.

Chae, B. J. et al. 'Effects of incremental levels of alpha-tocopherol acetate on performance, nutrient digestibility and meat quality of commercial broilers', Asian Australasian Journal of Animal Sciences. 2006, vol. 19, No. 2, pp. 203-208.

Database WPI—Week 201108, Thomson Scientific, London, GB, AN 2010-N41794 XP002727982 & CN101837 (2010).

De Wolfe, F.A. et al., "Ligand-binding proteins: their potential for application in systems for controlled delivery and uptake of ligands," Pharmacol. Rev. (2000) 52(2):207-236.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Devaraj, S. et al., "Modulation of monocyte-macrophage function with alpha-tocopherol: implications for atherosclerosis," Nat. Rev. (2002) 60(1):8-14.

Devaraj, S. et la., "Alpha tocopherol decreases CD36 expression in human monocyte-derived macrophages," J. Lipid Res. (2001) 42:521-527.

Dolfi, S. C. et al., "Inhibitory Effects of Different Forms of Tocopherols, Tocopherol Phosphates, and Tocopherol Quinones on Growth of Colon Cancer Cells," Journal of Agricultural and Food Chemistry, 2013, vol. 61, No. 36, pp. 8533-8540.

Ernster, L. et al., "Biochemical, physiological and medical aspects of ubiquinone function," Biochim. Biophys. Acta (1995) 1271:195-204.

Fracalossi, D.M. et al., "Oscars, Astronotus ocellatus, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Gann, P.H. et al., "Lower prostate cancer risk in men with elevated plasma lycopene levels: results of a prospective analysis," Cancer Res. (1999) 59(6):1225-1230.

Gavin, P. et al., "Transdermal deliver of various molecules in vivo using alpha-tocopheryl phosphate," Drug Delivery Today 2008) 8(9):34-41.

Ghayour-Mobarhan, M. et al., 'α-Tocopheryl Phosphate as a Bioactive Derivative of Vitamin E: A Review of the Literature', Journal of Dietary Supplements. 2014, vol. 12, No. 4, pp. 359-372.

Gianello, R. et al., "Subchronic oral toxicity study of mixed tocopheryl phosphates in rats," Int'l J. Toxicol. (2007) 26:475-490.

Gianello, R. et al., "α-tocopheryl phosphate: a novel, natural form of vitamin E," Free Radical Biol. Med. (2005) 39:970-976.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Guthrie et al., "VIIth Asian Conference of Nutrition: Lipid Symposium Proceedings," Journal of Nutrition, 1997, vol. 127, pp. 544s-548s.

Heinrichs, J., "Mastitis prevention: the nutritional approach," Feed Mix, 2008, vol. 16, No. 6, 3 pages.

Heron-Milhavet, L. et al., "Muscle-specific overexpression of CD36 reverses the insulin resistance and diabetes of MKR mice," Endocrinology (2004) 145:4667-4676.

Iimura, N. et al., "Complex formation between cationic surfactants and insoluble drugs," Bull. Chem. Soc. Jpn. (1999) 72:2417-2422.

Imada, I. et al., "Photochemical Reaction of Ubiquinone. IV. Coenzymatic activity of ubiquinone and related compounds," Chem. Pharm. Bull. (1965) 13:136-142.

International Specialty Products,"A Product Guide. Performance enhancing Products for Pharmaceuticals," (2005) 20 pages [retrieved on Jul. 27, 2010 from http://web.archive.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].

Isoda, K. et al., "Metformin inhibits proinflammatory responses and nuclear factor-κB in human vascular wall cells," Arterioscler. Thromb. Vasc. Biol. (2006) 26:611-617.

Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.

Jiang, Q. et al., "γ-tocopherol, the major form of vitamin E in the U.S. diet, deserves more attention," Am. J. Clin Nutri. (2001) 74(6):714-722.

Kagan, V. et al., "Antioxidant effects of ubiquinones in microsomes and mitochondria are mediated by tocopherol recycling," Biochem. Biophys. Res. Commun. (1990) 169(3):851-857.

(56) References Cited

OTHER PUBLICATIONS

Karrer, V.P. et al., "d,l-alpha-tocopherol-phosphorsaure-ester," Zurich, Chemisches Institut der Universitat (1933) p. 1137-1138, in German.
King, M.J. et al., "Transdermal delivery of insulin from a novel biphasic lipid system in diabetic rats," Diab. Tech. Therap. (2002) 4(4):479-488.
Knowler, W.C. et al., "Preventing Non-insulin-dependent diabetes," Diabetes (1995) 44:483-488.
Koh, "Antioxidants in a carotenoid-rich edible oil," Journal of Japan Mibyou System Association, 2003, vol. 9, No. 1, pp. 12-13.
Langsjoen, P.H. et al., "Overview of the use of CoQ10 in cardiovascular diseases," Biofactors (1999) 9:273-284.
Lass, A. et al., "Electron transport-linked ubiquinone-dependent recycling of α-tocopherol inhibits autooxidation of mitochondrial membranes," Arch. Biochem. Biophys. (1998) 352(2):229-236.
Lee, C-F et al., "Attenuation of UV-induced apoptosis by coenzyme Q10 in human cells harboring large-scale deletion of mitochondrial DNA," Ann. N.Y. Acad. Sci. (2005) 1042:429-438.
Lei, B. et al., Progress in alpha-tocopherol preparation technology, Xiandai Huagong (1997) 17(7):13-15.
Leira et al "Contact Dermatitis" 1992; 27:148-150.
Li et al., "Effect of HPMC and Carbopol on the release and floating properties of gastric floating drug delivery system using factorial design." International Journal of Pharmaceutics, 2003; 253:13-22.
Libinaki, R. et al., "Evaluation of the safety of mixed tocopheryl phosphates (MTP)—a formulation of α-tocopheryl phosphate plus α-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Madhavi et al., "Enhanced transdermal drug penetration of curcumin via ethosomes," Malaysian Journal of Pharmaceutical Sciences (2013) 11(1):49-58.
Magnusson et al., "Terpenes and ethanol enhance the transdermal permeation of the tripeptide thyrotropin releasing hormone in human epidermis," International Journal of Pharmaceutics 157, 1997, 113-121.
Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.
Maugard et al., "Synthesis of Water-Soluble Retinol Derivatives by Enzymatic Method," Biotechnol. Prog., 2002, vol. 18, pp. 424-428.
Mellors, A. et al., "The inhibition of mitochondrial peroxidation by ubiquinone and ubiquinol," J. Biol. Chem. (1966) 241(19):4353-4356.
Merck Index, The, "Fludarabine to Fludeoxyglucose F18" pages, Thirteenth Edition, Whitehouse Station, NJ (2001) pp. 729-730.
Merck Index, The, "α-estradiol" Thirteenth Edition, Whitehouse Station, NJ (2001) p. 660.
Min, J. et al., "Effect of apoptosis induced by different vitamin E homologous analogues in human hepatoma cells (HepG2)," J. Hygiene Res. China (2003) 32(4):343-345.
Miyamoto, S. et al., "Synthesis of a novel phosphate ester of a vitamin E derivative and its antioxidative activity," Biosci. Biotech. Biochem. (1998) 62(12):2463-2466.
Morgan, T.M. et al., "Transdermal delivery of estradiol in postmenopausal women with a novel topical aerosol," J. Pharm. Sci. (1998) 87(10):1226-1228.
Morgan, T.M. et al., "Enhanced transdermal delivery of sex hormones in swine with a novel topical aerosol," J. Pharm. Sci. (1998) 87(10):1219-1225.
Mortensen, S.A., "Perspectives on therapy of cardiovascular diseases with coenzyme Q10 (ubiquinone)," Clin. Investig. (1993) 71(Suppl.8):S116-S123.
Mottu, F. et al., "Organic solvents for pharmaceutical parenterals and embolic liquids: a review of toxicity data," PDA Journal of Pharm. Sci. Tech. (2000) 54(6):456-469.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Nakayama, S. et al., "Protective effects of a stable, water-soluble vitamin E on photodamage induced by UVB irradiation in cultured mouse skin," Photomedicine and Photobiology (1998) 20:99-100.
Negis, Y. et al., "Molecular mechanism of alpha-tocopheryl-phosphate transport across the cell membrane," Biochem. Biophys. Res. Comm. (2007) 359:348-353.
Negis, Y. et al., "On the existence of cellular tocopheryl phosphate, its synthesis, degradation and cellular roles: a hypothesis," IUBMB Life (2005) 57(1):23-25.
Negis, Y. et al., "The effect of tocopheryl phosphates on atherosclerosis progression in rabbits fed with a high cholesterol diet," Arch. Biochem. Biophys. (2006) 450:63-66.
Octoplus, "Formulation Development of Poorly Soluble Drugs" (www.octoplus.nl) (1999) 2 pages (downloaded Nov. 2008).
Ogru, E. et al., "Vitamin E phosphate: an endogenous form of vitamin E," Medimond S.r.l. (2003) 127-132.
Ostrenga, J. et al., "Significance of vehicle composition I: Relationship between topical vehicle composition, skin penetrability, and clinical efficacy," J. Pharm. Sci. (1971) 60(8):1175-1179.
Owens, D.R. et al., "Alternative routes of insulin delivery," Diabet. Med. (2003) 20:886-898.
Parker et al., "Neonatal vitamin K administration and childhood cancer in the North of England: retrospective case-control study," BMJ (1998) 316:189-193.
Pastori et al., "Lycopene in association with α-tocopherol inhibits at physiological concentrations proliferation of prostate carcinoma cells," Biochemical and Biophysical Research Communications, 1998, vol. 250, pp. 582-585.
Potts, R.O. et al., "Predicting skin permeability," Pharm. Res. (1992) 9(5):663-669.
Puratchikody, A. et al., "Reverse phase—high performance liquid chromatographic determination of atorvastatin calcium in solid dosage forms," Pharma. Review (2003) 1(2):79-80, 83—STN File CA, 139:399976.
Reference.com, "What are normal pH levels for the human stomach?" 2016, 1-5.
Rerek, M.E. et al., "Disodium lauriminodipropionate tocopheryl phosphates: a potent new anti-inflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
Ricciarelli, R. et al., "Vitamin E reduces the uptake of oxidized LDL by inhibiting CD36 scavenger receptor expression in cultured aortic smooth muscle cells," Circulation (2000) 102:82-87.
Rosenson et al., "Hypertriglyceridemia is associated with an elevated blood viscosity Rosenson: triglycerides and blood viscosity", Atherosclerosis, 2002, vol. 161, Issue 2, pp. 433-439.
Saikinnno (1991) 149-155, 195-198.
Saishinn (1984) 137-147, 190-201.
Sanghvi et al., "Solubility Improvement of Drug using N-Methyl Pyrrolidone," AAPS Pharm Sci Tech, 2008, vol. 9, No. 2, pp. 366-376.
Schwenke, D.C. et al., "α-tocopherol protects against diet induced atherosclerosis in New Zealand white rabbits," J. Lipid Res. (2002) 43:1927-1938.
Sevast'ianov, V.I. et al., "Transdermal delivery of insulin," Meditsinskaia Tekhnika (2003) 2:21-24.
Seyama, Y. et al., "Comparative effects of Vitamin K2 and estradiol on experiemental arteriosclerosis with diabetes mellitus," Int. J. Vitam. Nutr. Res. (2000) 70(6):301-304.
Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.

(56) References Cited

OTHER PUBLICATIONS

Singh, R.B. et al., "Randomized double-blind placebo-controlled trial of coenzyme Q10 in patients with acute myocardial infarction," Cardiov. Drugs Ther. (1998) 12:347-353.
Sinha, V.R. et al., "Coating polymers for colon specific drug delivery: A comparative in vitro evaluation," Acta. Pharm., 2003, vol. 53, pp. 41-47.
Spears, J.W. et al., "Role of antioxidants and trace elements in health and immunity of transition dairy cows,". The Veterinary Journal, 2008, 176:70-76.
Squillante et al, European Journal of Pharmaceutics and Biopharmaceutics 46 (1998) 265-271.
Stedman's Medical Dictionary, "Tocopherol," "Tocotrienol," and "Vitamin K1", 22nd Edition, Williams & Wilkins Co. (1972) p. 1303 and 1400.
Suzuki, T. et al., "The solution behavior and the association structure of long-chain monoalkyl phosphates," Chem. Soc. Japan (1986) 633-640, with English abstract.
Teupser, D. et al., "Alpha-tocopherol down-regulates scavenger receptor activity in macrophages," Atherosclerosis (1999) 144:109-115.
Traber, M.G. et al., "Human plasma vitamin E kinetics demonstrates rapid recycling of plasma RRR-alpha-tocopherol," Proc. Natl. Acad. Sci. USA (1994) 91:10005-10008.
Trommer et al., "Overcoming the Stratum Corneum: The Modulation of Skin Penetration," Skin Pharmacol Physiol, 2006, 19:106-121.
Visarius, T. et al., "Inhibition of human prostate cancer cell proliferation: vitamin E and lycopene targeted pathways regulating cell cycle progression," FASEB J. (2004) 18(8):C103.
Walters et al., "The effects of surfactants on penetration across the skin," Inter. J. Cosmetic Sci. (1993) 15:260-270.
Williams, A.C. et al., "Penetration enhancers," Advanced Drug Delivery Reviews (2004) 56(5):603-618.
Younis et al., "The prevention of type 2 diabetes mellitus: recent advances," Q.J. Med. (2004) 97:451-455.
Zia et al., Pharmaceutical Research, vol. 8, No. 4, 1991.
Zingg, J.-M. et al., 'α-Tocopheryl phosphate—An active lipid mediator?', Molecular Nutrition and Food Research. 2010, vol. 54, pp. 679-692.
United States Office Action for U.S. Appl. No. 09/979,436 dated Apr. 4, 2002 (6 pages).
United States Office Action for U.S. Appl. No. 09/979,436 dated Sep. 23, 2002 (6 pages).
United States Office Action for U.S. Appl. No. 10/416,775 dated Nov. 2, 2005 (10 pages).
United States Office Action for U.S. Appl. No. 10/416,775 dated Jun. 12, 2006 (10 pages).
United States Office Action for U.S. Appl. No. 10/416,775 dated Jul. 12, 2007 (11 pages).
United States Office Action for U.S. Appl. No. 10/416,775 dated Dec. 17, 2008 (6 pages).
United States Patent Office Action for U.S. Appl. No. 12/628,443 dated Feb. 18, 2011 (15 pages).
United States Patent Office Action for U.S. Appl. No. 12/628,443 dated Aug. 5, 2011 (8 pages).
United States Patent Office Notice of Allowance for U.S. Appl. No. 12/628,443 dated Jan. 12, 2012 (7 pages).
United States Office Action for U.S. Appl. No. 10/416,774 dated Sep. 6, 2007 (9 pages).
United States Office Action for U.S. Appl. No. 10/416,774 dated Jun. 11, 2008 (15 pages).
United States Office Action for U.S. Appl. No. 10/416,774 dated Feb. 17, 2009 (15 pages).
United States Office Action for U.S. Appl. No. 10/416,774 dated Apr. 15, 2009 (14 pages).
United States Patent Office Action for U.S. Appl. No. 10/416,774 dated Dec. 18, 2009 (11 pages).
United States Office Action for U.S. Appl. No. 10/462,480 dated Dec. 1, 2006 (10 pages).
United States Office Action for U.S. Appl. No. 10/462,480 dated Nov. 1, 2007 (10 pages).
United States Office Action for U.S. Appl. No. 10/462,480 dated Feb. 20, 2009 (17 pages).
United States Patent Office Action for U.S. Appl. No. 10/462,480 dated Nov. 27, 2009 (9 pages).
United States Patent Office Action for U.S. Appl. No. 12/768,307 dated Oct. 6, 2011 (13 pages).
United States Patent Office Action for U.S. Appl. No. 12/782,438 dated Aug. 30, 2012 (14 pages).
United States Office Action for U.S. Appl. No. 10/485,196 dated May 29, 2008 (23 pages).
United States Office Action for U.S. Appl. No. 10/485,196 dated Jul. 23, 2009 (9 pages).
United States Patent Office Action for U.S. Appl. No. 10/485,196 dated Jan. 25, 2010 (8 pages).
United States Patent Office Action for U.S. Appl. No. 10/485,196 dated Oct. 29, 2010 (13 pages).
United States Patent Office Notice of Allowance for U.S. Appl. No. 10/485,196 dated Apr. 14, 2011 (7 pages).
United States Office Action for U.S. Appl. No. 10/486,142 dated Mar. 18, 2008 (12 pages).
United States Patent Office Action for U.S. Appl. No. 12/212,803 dated Mar. 12, 2010 (13 pages).
United States Office Action for U.S. Appl. No. 10/487,743 dated Dec. 2, 2005 (22 pages).
United States Office Action for U.S. Appl. No. 10/487,743 dated Jul. 27, 2006 (23 pages).
United States Office Action for U.S. Appl. No. 10/498,684 dated Oct. 2, 2008 (21 pages).
United States Office Action for U.S. Appl. No. 10/498,684 dated Jun. 23, 2009 (19 pages).
United States Patent Office Action for U.S. Appl. No. 10/498,684 dated Jul. 7, 2010 (21 pages).
United States Office Action for U.S. Appl. No. 10/524,090 dated Mar. 12, 2008 (12 pages).
United States Office Action for U.S. Appl. No. 10/524,090 dated Mar. 3, 2010 (18 pages).
United States Patent Office Action for U.S. Appl. No. 10/524,090 dated Nov. 23, 2010 (19 pages).
United States Office Action for U.S. Appl. No. 10/542,511 dated Aug. 8, 2007 (19 pages).
United States Office Action for U.S. Appl. No. 10/542,511 dated Mar. 31, 2008 (20 pages).
United States Office Action for U.S. Appl. No. 10/542,511 dated Feb. 5, 2009 (23 pages).
United States Patent Office Action for U.S. Appl. No. 10/542,511 dated Jan. 12, 2010 (13 pages).
United States Patent Office Advisory Action for U.S. Appl. No. 10/542,511 dated May 25, 2010 (3 pages).
United States Patent Office Action for U.S. Appl. No. 12/834,553 dated Apr. 14, 2011 (13 pages).
United States Patent Office Action for U.S. Appl. No. 12/834,553 dated Oct. 7, 2011 (11 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 12/690,735 dated Sep. 27, 2011 (15 pages).
United States Patent Office Action for U.S. Appl. No. 12/690,735 dated Aug., 2, 2012 (9 pages).

(56) References Cited

OTHER PUBLICATIONS

United States Patent Office Action for U.S. Appl. No. 11/572,864 dated Mar. 15, 2012 (15 pages).
United States Patent Office Action for U.S. Appl. No. 11/572,864 dated Nov. 8, 2012 (16 pages).
United States Patent Office Action for U.S. Appl. No. 11/572,864 dated Sep. 16, 2013 (10 pages).
United States Patent Office Action for U.S. Appl. No. 11/572,864 dated Jun. 20, 2014 (11 pages).
United States Patent Office Action for U.S. Appl. No. 11/817,439 dated Nov. 24, 2010 (15 pages).
United States Patent Office Action for U.S. Appl. No. 11/817,439 dated May 11, 2011 (11 pages).
United States Patent Office Action for U.S. Appl. No. 11/817,439 dated Jul. 29, 2011 (2 pages).
United States Patent Office Action for U.S. Appl. No. 11/817,439 dated Nov. 7, 2012 (10 pages).
United States Patent Office Action for U.S. Appl. No. 11/817,453 dated Oct. 9, 2009 (11 pages).
United States Patent Office Action for U.S. Appl. No. 11/817,453 dated Aug. 2, 2010 (10 pages).
United States Patent Office Action for U.S. Appl. No. 11/817,453 dated Mar. 9, 2011 (12 pages).
United States Patent Office Action for U.S. Appl. No. 11/817,453 dated Oct. 13, 2011 (14 pages).
United States Patent Office Action for U.S. Appl. No. 11/817,453 dated Feb. 21, 2014 (13 pages).
United States Patent Office Action for U.S. Appl. No. 11/917,831 dated Jan. 19, 2011 (10 pages).
United States Patent Office Action for U.S. Appl. No. 11/917,831 dated Oct. 24, 2011 (11 pages).
United States Patent Office Action for U.S. Appl. No. 11/917,831 dated Oct. 3, 2014 (9 pages).
United States Patent Office Notice of Allowance for U.S. Appl. No. 11/917,831 dated Jul. 8, 2015 (7 pages).
United States Patent Office Action for U.S. Appl. No. 12/158,932 dated Aug. 19, 2010 (15 pages).
United States Patent Office Action for U.S. Appl. No. 13/501,494 dated Dec. 18, 2012 (13 pages).
United States Patent Office Final Rejection for U.S. Appl. No. 13/501,494 dated Aug. 22, 2013 (13 pages).
United States Patent Office Action for U.S. Appl. No. 13/501,494 dated Apr. 21, 2014 (19 pages).
United States Patent Office Action for U.S. Appl. No. 13/501,494 dated Nov. 18, 2014 (16 pages).
United States Patent Office Action for U.S. Appl. No. 13/501,494 dated Jan. 26, 2016 (20 pages).
United States Patent Office Action for U.S. Appl. No. 15/218,719 dated Sep. 25, 2017 (12 pages).
United States Patent Office Action for U.S. Appl. No. 13/501,498 dated Feb. 21, 2013 (12 pages).
United States Patent Office Final Rejection for U.S. Appl. No. 13/501,498 dated Nov. 14, 2013 (10 pages).
United States Patent Office Action for U.S. Appl. No. 13/501,498 dated Nov. 21, 2014 (9 pages).
United States Patent Office Final Rejection for U.S. Appl. No. 13/501,498 dated Apr. 8, 2015 (16 pages).
United States Patent Office Action for U.S. Appl. No. 13/501,498 dated Dec. 4, 2015 (10 pages).
United States Patent Office Action for U.S. Appl. No. 13/501,498 dated Jun. 9, 2016 (14 pages).
United States Patent Office Action for U.S. Appl. No. 15/261,455 dated Feb. 27, 2017 (12 pages).
United States Patent Office Action for U.S. Appl. No. 15/261,455 dated Sep. 6, 2017 (10 pages).
United States Patent Office Action for U.S. Appl. No. 15/261,455 dated Mar. 22, 2018 (6 pages).
United States Patent Office Action for U.S. Appl. No. 15/261,455 dated Dec. 11, 2018 (20 pages).
United States Patent Office Action for U.S. Appl. No. 12/782,560 dated Sep. 1, 2011 (18 pages).
United States Patent Office Action for U.S. Appl. No. 12/782,560 dated May 24, 2012 (22 pages).
United States Patent Office Action for U.S. Appl. No. 13/501,499 dated Sep. 25, 2013 (12 pages).
United States Patent Office Action for U.S. Appl. No. 13/683,698 dated Apr. 24, 2013 (18 pages).
United States Patent Office Final Rejection for U.S. Appl. No. 13/683,698 dated Nov. 14, 2013 (15 pages).
United States Patent Office Action for U.S. Appl. No. 13/683,698 dated Jun. 20, 2014 (17 pages).
United States Patent Office Final Rejection for U.S. Appl. No. 13/683,698 dated Jan. 29, 2015 (17 pages).
United States Patent Office Action for U.S. Appl. No. 13/683,698 dated Sep. 1, 2015 (19 pages).
United States Patent Office Action for U.S. Appl. No. 12/782,564 dated Sep. 1, 2011 (20 pages).
United States Patent Office Action for U.S. Appl. No. 12/782,564 dated May 24, 2012 (25 pages).
United States Patent Office Action for U.S. Appl. No. 13/501,500 dated Dec. 17, 2012 (14 pages).
United States Patent Office Notice of Allowance for U.S. Appl. No. 13/501,500 dated Aug. 21, 2013 (11 pages).
United States Patent Office Action for U.S. Appl. No. 14/086,738 dated May 22, 2014 (14 pages).
United States Patent Office Action for U.S. Appl. No. 14/550,514 dated Apr. 23, 2015 (13 pages).
United States Patent Office Notice of Allowance for U.S. Appl. No. 14/550,514 dated Dec. 10, 2015 (6 pages).
United States Patent Office Action for U.S. Appl. No. 15/065,510 dated Dec. 12, 2016 (14 pages).
United States Patent Office Action for U.S. Appl. No. 13/577,124 dated Feb. 14, 2013 (15 pages).
United States Patent Office Final Rejection for U.S. Appl. No. 13/577,124 dated Aug. 2, 2013 (14 pages).
United States Patent Office Action for U.S. Appl. No. 13/577,124 dated Dec. 26, 2014 (9 pages).
United States Patent Office Final Rejection for U.S. Appl. No. 13/577,124 dated Jul. 22, 2015 (11 pages).
United States Patent Office Action for U.S. Appl. No. 13/577,124 dated Jun. 16, 2016 (8 pages).
United States Patent Office Final Rejection for U.S. Appl. No. 13/577,124 dated Nov. 15, 2016 (10 pages).
United States Patent Office Action for U.S. Appl. No. 14/004,973 dated Apr. 9, 2015 (12 pages).
United States Patent Office Final Rejection for U.S. Appl. No. 14/004,973 dated Oct. 20, 2015 (14 pages).
United States Patent Office Action for U.S. Appl. No. 14/004,973 dated Apr. 13, 2016 (13 pages).
United States Patent Office Notice of Allowance for U.S. Appl. No. 14/004,973 dated Sep. 28, 2016 (5 pages).
United States Patent Office Action for U.S. Appl. No. 15/400,356 dated Oct. 19, 2017 (12 pages).
United States Patent Office Action for U.S. Appl. No. 15/400,356 dated Feb. 22, 2018 (12 pages).
International Search Report and Written Opinion for Application No. PCT/AU2010/001719 dated Mar. 8, 2011 (11 pages).
International Preliminary Report on Patentability for Application No. PCT/AU2010/001719 dated Nov. 11, 2011 (6 pages).
International Search Report and Written Opinion for Application No. PCT/AU2011/000122 dated Apr. 6, 2011 (14 pages).
Written Opinion for Application No. PCT/AU2011/000122 dated Jan. 3, 2012 (4 pages).
International Preliminary Report on Patentability for Application No. PCT/AU2011/000122 dated Mar. 13, 2012.
International Search Report and Written Opinion for Application No. PCT/AU2010/000580 dated Jun. 29, 2010 (8 pages).
International Preliminary Report on Patentability for Application No. PCT/AU2010/000580 dated Feb. 20, 2012 (5 pages).
International Search Report and Written Opinion for Application No. PCT/AU2011/000358 dated May 31, 2011 (10 pages).

(56) References Cited

OTHER PUBLICATIONS

Written Opinion for Application No. PCT/AU2011/000358 dated Feb. 21, 2012 (7 pages).
International Search Report and Written Opinion for Application No. PCT/AU2011/000112 dated Feb. 25, 2011 (8 pages).
International Preliminary Report on Patentability for Application No. PCT/AU2011/000112 dated Mar. 13, 2012.
International Search Report for Application No. PCT/AU2012/000220 dated Apr. 2, 2012 (2 pages).
Written Opinion for Application No. PCT/AU2012/000220 dated Apr. 2, 2012 (3 pages).
International Search Report for Application No. PCT/AU2017/051381 dated Feb. 13, 2018 (7 pages).
International Search Report for Application No. PCT/AU2017/051363 dated Jan. 25, 2018 (8 pages).
International Search Report for Application No. PCT/AU2016/051209 dated Feb. 2, 2017 (12 pages).
International Preliminary Report of Patentability for Application No. PCT/AU2016/051209 dated Mar. 22, 2018.
European Patent Office Extended Search Report for Application No. 16871823.7 dated Jun. 21, 2019 (6 pages).
United States Patent Office Action for U.S. Appl. No. 16/438,245 dated Nov. 29, 2019 (9 pages).
English Machine Translation of CN101524330A, published Sep. 9, 2009.
Chinese Patent Office Action for Application No. 201680072343.6 dated Apr. 16, 2020 (30 pages, English translation Included).
Russian Patent Office Action for Application No. 2018121981/04 dated Mar. 24, 2020 (15 pages, English translation included).
United States Patent Office Action for U.S. Appl. No. 16/467,759 dated Sep. 3, 2020 (11 pages).
United States Patent Office Action for U.S. Appl. No. 16/470,943 dated Dec. 8, 2020 (6 pages).
United States Patent Office Action for U.S. Appl. No. 16/467,759 dated Dec. 21, 2020 (11 pages).

\* cited by examiner

PHARMACEUTICAL FORMULATION

CROSS-REFERENCE TO RELATED APPLICATIONS

This patent application is a national stage filing under 35 U.S.C. 371 of International Application No. PCT/AU2016/051209, filed Dec. 9, 2016 which claims foreign priority to Australian Patent Application No. 2015905089, filed Dec. 9, 2015, and U.S. Provisional Application No. 62/329,166, filed Apr. 28, 2016, the disclosures of which are incorporated by reference herein in their entireties. Priority to each application is hereby claimed.

TECHNICAL FIELD

The invention relates to a formulation, more particularly a pharmaceutical formulation.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Drug delivery technologies have been developed to improve bioavailability, safety, duration, onset or release, of an active agent.

When developing drug delivery technologies, problems likely to be encountered include compatibility of the drug delivery system and the active agent, maintaining an adequate and effective duration, potential for side effects, and meeting patient convenience and compliance. As a consequence, many drug delivery technologies fall short of desired improvements and requirements. There is a need for improved or alterative drug technologies.

SUMMARY

Accordingly, a first aspect of the present invention provides a formulation comprising a primary surfactant, a tocol phosphate, water, an active agent, and optionally an oil, wherein the active agent and/or the optional oil comprises a hydrophobic phase.

DESCRIPTION

The invention relates to a formulation comprising a primary surfactant, a tocol phosphate, water, an active agent, and optionally an oil, wherein the active agent and/or the optional oil comprises a hydrophobic phase.

Active Agent

The term "active agent" refers to a chemical substance that has an effect in or on humans or animals for medical, therapeutic, cosmetic and veterinary purposes, and encompasses drugs, pharmaceuticals, cosmeceuticals, nutraceuticals and nutritional agents. It will be appreciated that some of active agents can be classified in more than one of these classes.

In certain embodiments, the active agent is insoluble in water or sparingly soluble in water.

In some embodiments, the active agent is selected from the group consisting of amprenavir, bexarotene, calcitriol, clofazimine, cyclosporine (or cyclosporin), digoxin, doxercalciferol, dronabinol, dutasteride, etoposide, isotretinoin, itraconazole, lopinavir, ritonavir, loratadine, nifedipine, nimodipine, phenobarbital, progesterone, risperidone, saquinavir, sirolimus, tretinoin, valproic acid, amiodarone HCl, chlordiazepoxide HCl, diazepam, dihydroergotamine mesylate, fenoldopam, oxytetracycline, paricalcitrol, pentobarbital sodium, phenytoin sodium, phytonadione, propofol, ziprasidone mesylate, docetaxel, etoposide, fulvestrant, haloperidol decanoate, leuprolide acetate, viadur, lorazepam, paclitaxel, tacrolimus, teniposide, testosterone enanthate, testosterone cypionate, estradiol cypionate, and valrubicin.

In one embodiment, the active agent is propofol.

In some embodiments, the formulation is suitable for active agents that are considered oils. In other embodiments, the formulation is suitable for active agents that are not considered oils.

In some embodiments, the active agent may present in an amount within the range of about 1 mg/mL to about 20 mg/mL of the total amount of the formulation. In some embodiments, the active agent may present in an amount within the range of about 1 mg/mL to about 10 mg/mL of the total amount of the formulation. In yet other embodiments, the active agent may present in an amount within the range of about 5 mg/mL to about 10 mg/mL of the total amount of the formulation. In one embodiment, the active agent is present in an amount of about 10 mg/mL of the total amount of the formulation. In another embodiment, the active agent is present in an amount of about 5 mg/mL of the total amount of the formulation. In yet another embodiment, the active agent is present in an amount of about 2 mg/mL of the total amount of the formulation. In still another embodiment, the active agent is present in an amount of about 1 mg/mL of the total amount of the formulation.

Surfactants

The primary surfactant may be a non-ionic, anionic, cationic or zwitterionic surfactant.

In some embodiments, the primary surfactant is a non-ionic surfactant. Suitable non-ionic surfactants include, but are not limited to, polyethylene glycol, propylene glycol, polyethoxylated castor oil (e.g. Cremophor® EL), hydrogenated castor oil (e.g. Cremophor® RH 60), 2-hydroxyethyl 12-hydroxyoctadecanoate (e.g. Solutol® HS 15), polyoxyethylene monooleate (e.g. PEG monoleate), polyoxythylene monostearate (e.g. PEG 400 monostearate), polyoxythylene monolaurate (e.g. PEG 400 monolaurate), sorbitan monolaurate (e.g. Span® 20), triethanolamine oleate, polyoxythylene sorbitan monolaurate (e.g. Tween® 20, Tween 21), polyoxythylene sorbitan monopalmitate (e.g. Tween® 40), polyoxythylene sorbitan monostearate (e.g. Tween® 60, Tween® 61), polyoxythylene sorbitan tristearate (e.g. Tween® 65), polyoxythylene sorbitan monooleate (e.g. Tween® 80, Tween® 81) and polyoxythylene sorbitan trioleate (e.g. Tween® 85).

In some embodiments, the primary surfactant has an HLB value of from 8 to 18. In other embodiments, the primary surfactant has an HLB value of from 8 to 14. Examples of surfactants having a HLB value within this range include, but are not limited to, polyethylene glycol, propylene glycol, polyethoxylated castor oil (e.g. Cremophor® EL), hydrogenated castor oil (e.g. Cremophor® RH 60), 2-hydroxyethyl 12-hydroxyoctadecanoate (e.g. Solutol® HS 15), sodium oleate, polyoxyethylene monooleate (e.g. PEG monoleate), polyoxythylene monostearate (e.g. PEG 400 monostearate), polyoxythylene monolaurate (e.g. PEG 400 monolaurate), sorbitan monolaurate (e.g. Span® 20), triethanolamine oleate, polyoxythylene sorbitan monolaurate (e.g. Tween® 20, Tween 21), polyoxythylene sorbitan monopalmitate (e.g. Tween® 40), polyoxythylene sorbitan monostearate (e.g. Tween® 60, Tween® 61), polyoxythylene sorbitan tristearate (e.g. Tween® 65), polyoxythylene sorbitan monooleate (e.g. Tween® 80, Tween® 81) and polyoxythylene sorbitan trioleate (e.g. Tween® 85).

In some embodiments, the primary surfactant is polyoxythylene sorbitan monooleate (e.g. Tween® 80).

In some embodiments, only one primary surfactant is used. However, in other embodiments, a combination of primary surfactants may be used. For example, a combination of polyoxythylene sorbitan monooleate (e.g. Tween® 80) with another primary surfactant.

The primary surfactant may be present in an amount within the range of about 1% w/w to about 30% w/w of the total amount of the formulation. In some embodiments, the primary surfactant may be present in an amount within the range of about 1% w/w to about 20% w/w of the total amount of the formulation. In other embodiments, the primary surfactant may be present in an amount within the range of about 1% w/w to about 10% w/w of the total amount of the formulation. In further embodiments, the primary surfactant may be present in an amount within the range of about 10% w/w to about 20% w/w of the total amount of the formulation. In one embodiment, the primary surfactant may be present in an amount of about 20% w/w of the total amount of the formulation. In another embodiment, the primary surfactant may be present in an amount of about 10% w/w of the total amount of the formulation.

In one embodiment, the ratio of the surfactant to the active agent is greater than 10:1. In these embodiments, it has been found that such a ratio results in a clear solution.

Tocol Phosphate

The tocol phosphate may be selected from the group consisting of tocopheryl phosphates and/or tocotrienol phosphates, including salts thereof. In the present formulation, the tocol phosphate may act as a co-surfactant generally required for forming a micro-emulsion.

Examples of a tocol phosphate include, but are not limited to, mono-(tocopheryl) phosphate, mono-(tocopheryl) phosphate monosodium salt, mono-(tocopheryl) phosphate disodium salt, di-(tocopheryl) phosphate, di-(tocopheryl) phosphate monosodium salt, mono-(tocotrienol) phosphate, mono-(tocotrienol) phosphate monosodium salt, mono-(tocotrienol) phosphate disodium salt, di-(tocotrienol) phosphate, di-(tocotrienol) phosphate monosodium salt. The tocol phosphate may also be a mixture of a tocopheryl phosphate and/or a tocotrienol phosphate. For example, a mixture of a mono-(tocopheryl) phosphate and di-(tocopheryl) phosphate ("TPM").

The "salts" may include metal salts such as alkali or alkaline earth metal salts, for example sodium, magnesium, potassium and calcium salts. Sodium and potassium salts are preferred.

The tocol phosphate may or may not be neutralised. If neutralised, it is neutralised to near neutral pH, more preferably within a pH range of 5-7.

The tocol phosphate may be prepared as a solution prior to inclusion in the formulation. Suitable solvents include any water miscible solvents, for example, alcoholic solvents. Suitable alcoholic solvents include C1-C6 alcohols, preferably ethanol or isopropanol. In some embodiments, the tocol phosphate solution may be prepared using up to 2.5% alcoholic solvent.

The formulation may comprise a tocol phosphate in an amount within the range of about 0.01% w/w to about 5% w/w of the total amount of the formulation. In some embodiments, the formulation may comprise a tocol phosphate in an amount within the range of about 0.03% w/w to about 0.15% w/w of the total amount of the formulation. In one embodiment, the formulation may comprise a tocol phosphate in an amount of about 0.03% w/w of the total amount of the formulation. In another embodiment, the formulation may comprise a tocol phosphate in an amount of about 0.125% w/w of the total amount of the formulation.

Optional Oil

A formulation of the present invention may also comprise an optional oil. The oil may be any oil suitable for pharmaceutical products.

In some embodiments, the oil is a plant or vegetable oil, such as, for example, canola oil, cotton seed oil, sesame oil, corn oil, sunflower oil, safflower oil and soybean oil.

The oil may also be selected from mineral oils or synthetic oils such as mono- or di-glycerides of fatty acids and medium-chain triglycerides.

Excipients

A formulation of the present invention can optionally further comprise one or more excipients. A person skilled in the art of the invention would appreciate suitable excipients that could be included in formulations of the present invention, e.g. one or more stabilizers. The choice and amount of excipients will depend on the intended use of formulations, the mode of administration and/or the dosage form.

Preparation

The formulation may be prepared by a variety of techniques. For instance, the formulations could be prepared by any methods well known in the art of pharmacy such as described in Remington J. P., The Science and Practice of Pharmacy, ed. A. R. Gennaro, $20^{th}$ edition, Lippincott, Williams and Wilkins Baltimore, Md. (2000).

One method of preparing the formulation involves combining the active agent and/or optional oil with the primary surfactant and tocol phosphate or a solution of tocol phosphate in alcoholic solvent, and then adding water.

The formulation may optionally further comprise one or more excipients known in the art (e.g. a stabilizer).

The pH of the formulation may optionally be adjusted with a suitable acid or base, or by the use of a buffering agent in the aqueous phase. An example of a suitable base for adjusting the pH is NaOH. Examples of suitable buffering agents include phosphate buffer and citrate buffer. In one embodiment, the pH of the formulation is adjusted immediately upon addition of the aqueous phase.

In some embodiments, the pH of the formulation is, or is adjusted to be, within the range of 4-10.

The components are then mixed, likely to form an emulsion. In some embodiments, the components are mixed using standard mixing equipment. In other embodiments, the components are mixed using high shear mixing.

If the active agent is considered an oil, it may comprise or be the hydrophobic phase. In these embodiments, the hydrophobic phase may not also comprise the optional oil. If the active agent is not considered an oil, the formulation may also comprise an oil. The optional oil may comprise or be the hydrophobic phase. In such embodiments, the hydrophobic phase may also comprise the active agent. The active agent may alternatively, or in addition, be present in an aqueous phase.

Compositions comprising oil and water usually result in an emulsion. Accordingly, the formulation of the present invention may be an emulsion. However, it has been found that the presence of a tocol phosphate may modify an oil-and-water to be a micro-emulsion or a nano-emulsion.

Therefore, in some embodiments, the emulsion may be a micro-emulsion or a nano-emulsion.

Generally, a "micro-emulsion" is thermodynamically stable. The micro-emulsions of the present invention are transparent and therefore the particle size would be below the visible range. According to literature in the art, the non-visible particle sizes are within the range 5-50 nm and visible particle sizes are within the range 50-200 nm. A clear formulation may be considered aesthetically superior, compared to a cloudy formulation. Further, as a micro-emulsion, the formulation of the present invention is unlikely to require the presence of a stabilizer. However, in some embodiments, the formulation may also comprise a stabilizer.

Routes of Administration

Routes of administration can broadly be divided into a three categories by effect, namely, "topical" where the desired effect is local, so the substance is applied directly where its action is desired, "enteral" where the desired effect is systemic (non-local) so the substance is given via the digestive tract, and "parenteral" where the desired effect is systemic, so the substance is given by routes other than the digestive tract.

The formulation of the present invention is suitable for topical, enteral or parenteral administration.

It is considered that the formulation would be most suitable for parenteral administration, more particularly as an injectable formulation.

Examples of topical routes of administration having a local effect include epicutaneous (onto the skin).

Examples of enteral routes of administration having a systemic (non-local) effect include any form of administration that involves any part of the gastrointestinal tract, such as oral (into the mouth), intranasal (into the nose), rectal (into the rectum), and vaginal (into the vagina). Oral administration includes buccal administration (absorbed through the cheek near the gumline), and sublingual administration (under the tongue).

Examples of parenteral routes of administration by injection, infusion or diffusion having a systemic effect include intravenous (into a vein), intraarterial (into an artery), intramuscular (into a muscle), intracardiac (into the heart), subcutaneous (under the skin), percutaneous (via needle-puncture into the skin), intradermal (into the skin itself), intrathecal (into the spinal canal), intraperitoneal (infusion or injection into the peritoneum), intravesical infusion (infusion into the urinary bladder), epidural (injection or infusion into the epidural space), transdermal or transcutaneous (diffusion through the intact skin), transmucosal (diffusion through a mucous membrane), insufflation (diffusion through the nose), inhalational (diffusion through the mouth), and intramammary (into mammary tissue).

In this specification, except where the context requires otherwise, the words "comprise", "comprises", and "comprising" mean "include", "includes", and "including" respectively, i.e. when the invention is described or defined as comprising specified features, various embodiments of the same invention may also include additional features.

EXAMPLES

Various embodiments/aspects of the present invention will now be described with reference to the following non-limiting examples.

Example 1

The following micro-emulsions were prepared by adding a tocol phosphate to an active agent, then adding a primary surfactant and then adding water, followed by stirring for 5-10 minutes with little to no shaking.

| | |
|---|---|
| Propofol | 10 mg/mL |
| Tween ® 80 | 10% w/w |
| A mixture of a mono-(tocopheryl) phosphate and di-(tocopheryl) phosphate | 0.03% w/w |
| Water | balance |
| Propofol | 10 mg/mL |
| Tween ® 80 | 20% w/w |
| A mixture of a mono-(tocopheryl) phosphate and di-(tocopheryl) phosphate | 0.03% w/w |
| Water | balance |
| Propofol | 10 mg/mL |
| Tween ® 80 | 30% w/w |
| A mixture of a mono-(tocopheryl) phosphate and di-(tocopheryl) phosphate | 0.03% w/w |
| Water | balance |
| Propofol | 10 mg/mL |
| Tween ® 80 | 10% w/w |
| A mixture of a mono-(tocopheryl) phosphate and di-(tocopheryl) phosphate | 0.05% w/w |
| Water | balance |
| Propofol | 10 mg/mL |
| Tween ® 80 | 20% w/w |
| A mixture of a mono-(tocopheryl) phosphate and di-(tocopheryl) phosphate | 0.05% w/w |
| Water | balance |
| Propofol | 10 mg/mL |
| Tween ® 80 | 30% w/w |
| A mixture of a mono-(tocopheryl) phosphate and di-(tocopheryl) phosphate | 0.05% w/w |
| Water | balance |
| Propofol | 10 mg/mL |
| Tween ® 80 | 10% w/w |
| A mixture of a mono-(tocopheryl) phosphate and di-(tocopheryl) phosphate | 0.1% w/w |
| Water | balance |
| Propofol | 10 mg/mL |
| Tween ® 80 | 20% w/w |
| A mixture of a mono-(tocopheryl) phosphate and di-(tocopheryl) phosphate | 0.1% w/w |
| Water | balance |
| Propofol | 10 mg/mL |
| Tween ® 80 | 30% w/w |
| A mixture of a mono-(tocopheryl) phosphate and di-(tocopheryl) phosphate | 0.1% w/w |
| Water | balance |

In each of the above formulations, the tocol phosphate (i.e. a mixture of a mono-(tocopheryl) phosphate and di-(tocopheryl) phosphate) was provided in either ethanol or isopropanol in an amount of 2.5% final concentration.

Example 2

The following micro-emulsions were prepared by dissolving a mixture of a mono-(tocopheryl) phosphate and di-(tocopheryl) phosphate (TPM) in ethanol (EtOH), adding Tween® 80 (T-80) and mixing. Water was then added and the pH was adjusted, as necessary. The formulations were mixed for 24 hours.

| Formulation ID | % T-80 | Propofol | % TPM (solvent) | % QS | 1M NaOH | pH Water | Appearance |
|---|---|---|---|---|---|---|---|
| A1 | 10 | 10 mg/mL | 0.1% TPM (EtOH) | 88.4 | 0 µL | 4.70 | Clear |
| A2 | 10 | 10 mg/mL | 0.1% TPM (EtOH) | 88.4 | 5 µL | 6.56 | Clear |
| A3 | 10 | 10 mg/mL | 0.1% TPM (EtOH) | 88.4 | 10 µL | 8.27 | Clear |
| A4 | 10 | 10 mg/mL | 0.1% TPM (EtOH) | 88.4 | 20 µL | 9.53 | Clear |

-continued

| Formulation ID | % T-80 | Propofol | % TPM (solvent) | % QS | 1M NaOH | pH Water | Appearance |
|---|---|---|---|---|---|---|---|
| B1 | 10 | 10 mg/mL | 0.1% TPM (EtOH) | 88.5 | 0 µL | 4.30 | Clear |
| B2 | 10 | 10 mg/mL | 0.1% TPM (EtOH) | 88.5 | 5 µL | 5.29 | Clear |
| B3 | 10 | 10 mg/mL | 0.1% TPM (EtOH) | 88.5 | 10 µL | 7.38 | Clear |
| B4 | 10 | 10 mg/mL | 0.1% TPM (EtOH) | 88.5 | 20 µL | 8.51 | Clear |
| C1 | 10 | 10 mg/mL | 0.1% TPM (IPA) | 88.4 | 0 µL | 4.56 | Clear |
| C2 | 10 | 10 mg/mL | 0.1% TPM (IPA) | 88.4 | 5 µL | 6.37 | Clear |
| C3 | 10 | 10 mg/mL | 0.1% TPM (IPA) | 88.4 | 10 µL | 7.25 | Clear (Pink) |
| C4 | 10 | 10 mg/mL | 0.1% TPM (IPA) | 88.4 | 20 µL | 8.89 | Clear (Pink) |
| D1 | 20 | 20 mg/mL | 0.1% TPM (EtOH) | 77.4 | 0 µL | 5.06 | Clear |
| D2 | 20 | 20 mg/mL | 0.1% TPM (EtOH) | 77.4 | 5 µL | 5.68 | Clear |
| D3 | 20 | 20 mg/mL | 0.1% TPM (EtOH) | 77.4 | 10 µL | 6.44 | Clear |
| D4 | 20 | 20 mg/mL | 0.1% TPM (EtOH) | 77.4 | 20 µL | 6.87 | Clear |
| E1 | 20 | 20 mg/mL | 0.1% TPM (EtOH) | 77.5 | 0 µL | 4.84 | Clear |
| E2 | 20 | 20 mg/mL | 0.1% TPM (EtOH) | 77.5 | 5 µL | 5.63 | Clear |
| E3 | 20 | 20 mg/mL | 0.1% TPM (EtOH) | 77.5 | 10 µL | 6.08 | Clear |
| E4 | 20 | 20 mg/mL | 0.1% TPM (EtOH) | 77.5 | 20 µL | 7.06 | Clear (Pink) |
| F1 | 20 | 20 mg/mL | 0.1% TPM (IPA) | 77.4 | 0 µL | 5.03 | Clear |
| F2 | 20 | 20 mg/mL | 0.1% TPM (IPA) | 77.4 | 5 µL | 5.47 | Clear |
| F3 | 20 | 20 mg/mL | 0.1% TPM (IPA) | 77.4 | 10 µL | 6.22 | Clear |
| F4 | 20 | 20 mg/mL | 0.1% TPM (IPA) | 77.4 | 20 µL | 7.22 | Clear (Pink) |
| G1 | 10 | 20 mg/mL | 0.1% TPM (EtOH) | 87.4 | 0 µL | 4.89 | Opaque |
| G2 | 10 | 20 mg/mL | 0.1% TPM (EtOH) | 87.4 | 5 µL | 5.68 | Opaque |
| G3 | 10 | 20 mg/mL | 0.1% TPM (EtOH) | 87.4 | 10 µL | 6.13 | Opaque |
| G4 | 10 | 20 mg/mL | 0.1% TPM (EtOH) | 87.4 | 20 µL | 7.14 | Opaque |
| H1 | 10 | 20 mg/mL | 0.1% TPM (EtOH) | 87.5 | 0 µL | 4.97 | Opaque |
| H2 | 10 | 20 mg/mL | 0.1% TPM (EtOH) | 87.5 | 5 µL | 5.32 | Opaque |
| H3 | 10 | 20 mg/mL | 0.1% TPM (EtOH) | 87.5 | 10 µL | 6.09 | Opaque |
| H4 | 10 | 20 mg/mL | 0.1% TPM (EtOH) | 87.5 | 20 µL | 7.38 | Opaque |

It was initially thought that adjusting the pH to 7 would clarify a formulation (hence the above measurements). However, it was observed that keeping the native pH was effective in maintaining a transparent formulation.

The formulations B1, E1 and H1 were selected for preparation in a larger scale (100 g).

Example 3

The following micro-emulsions were prepared by preparing a stock concentration of TPM in EtOH, then adding Tween® 80 (T-80), followed by propofol, stirring until homogenous and then adding water.

The stock concentration of TPM in EtOH was prepared by dissolving 2.5 grams of TPM with 10 grams of EtOH in a 20 mL glass scintillation vial. The TPM/EtOH stock concentration solution was left to dissolve by stirring overnight on a 40° C. magnetic hot plate.

The following methodology was applied according to the amounts specified in Table 1 (see below).

Pipette 'x' grams of the TPM/EtOH stock solution (prepared above) into a 100 mL glass jar, followed by adding 'x' grams of T-80.

Then add 'x' grams of propofol to the TPM/EtOH/T-80 preparation and stir on the hot plate at 40° C. until homogenous.

Add quantity sufficient MilliQ water so that the final formulation is 100 grams.

Leave overnight on the magnetic plate stirring.

TABLE 1

| | Formulation components | | | |
|---|---|---|---|---|
| | B1 | E1 | H1 | Z1 |
| TPM/EtOH Stock | 0.5 grams | 0.5 grams | 0.5 grams | 0.5 grams |
| T-80 | 10 grams | 20 grams | 10 grams | 20 grams |
| Propofol | 1 gram | 2 grams | 2 grams | 1 gram |
| QS MilliQ Water | 88.5 grams | 77.5 grams | 87.5 grams | 78.5 grams |

Results

After formulating in a 100 mL glass jar, 20 mL of each was aliquoted into small vials.

According to the naked-eye, formulation B1 showed the most clarity, whilst formulation H1 showed the least. The results are shown in the table below.

| | B1 | E1 | H1 | Z1 |
|---|---|---|---|---|
| Appearance | Clear | Yellow | Milky | Yellow |

CONCLUSION

The issue of opacity was considered and was addressed by the action of TPM, in that, it kept the propofol in suspension and most importantly prevented oil droplets from forming in the formulation. This was interpreted as being the case for formulation B1, due to the fact that the formulation was clear in appearance.

Although this invention has been described by example and with reference to possible embodiment thereof, it is to be understood that modifications or improvements may be made thereto without departing from the scope of the invention.

The invention claimed is:

1. An emulsion comprising 10 mg/mL propofol, 20% w/w polyoxyethylene sorbitan monooleate, 0.05% w/w solution of a mixture of mono-(tocopheryl) phosphate and di-(tocopheryl) phosphate in ethanol, and balance of water.

2. An emulsion comprising 10 mg/mL propofol, 1-10% w/w polyoxyethylene sorbitan monooleate, 0.01 to 5% w/w mixture of mono-(tocopheryl) phosphate and di-(tocopheryl) phosphate in ethanol, and balance of water.

3. An emulsion comprising 10 mg/mL propofol, 1-10% w/w polyoxyethylene sorbitan monooleate, 0.03 to 0.15% w/w mixture of mono-(tocopheryl) phosphate and di-(tocopheryl) phosphate in ethanol, and balance of water.

* * * * *